(12) United States Patent
Brännström

(10) Patent No.: US 7,728,606 B2
(45) Date of Patent: Jun. 1, 2010

(54) MEASUREMENT INSTRUMENT

(76) Inventor: Roland Brännström, Jonseredsgatan 7, S-416 70 Göteborg (SE)

( * ) Notice: Subject to any disclaimer, the term of this patent is extended or adjusted under 35 U.S.C. 154(b) by 230 days.

(21) Appl. No.: 11/916,681

(22) PCT Filed: May 26, 2006

(86) PCT No.: PCT/SE2006/000615

§ 371 (c)(1),
(2), (4) Date: Dec. 6, 2007

(87) PCT Pub. No.: WO2006/135302

PCT Pub. Date: Dec. 21, 2006

(65) Prior Publication Data

US 2008/0209987 A1 Sep. 4, 2008

(30) Foreign Application Priority Data

Jun. 13, 2005 (SE) .................................... 0501340

(51) Int. Cl.
*G01N 33/00* (2006.01)
(52) U.S. Cl. ...................... 324/654; 324/658; 73/61.41; 73/61.42; 73/61.43
(58) Field of Classification Search ................... 324/654
See application file for complete search history.

(56) References Cited

U.S. PATENT DOCUMENTS

| 4,078,863 A | 3/1978 | Eriksson et al. |
| 4,201,471 A | 5/1980 | Pitt et al. |
| 5,005,402 A * | 4/1991 | Pischinger et al. .......... 324/663 |
| 5,033,289 A * | 7/1991 | Cox .......................... 73/61.43 |

(Continued)

FOREIGN PATENT DOCUMENTS

| GB | 2131553 A | 12/1984 |
| WO | 2004026129 A1 | 4/2004 |

OTHER PUBLICATIONS

International Preliminary Report on Patentability for corresponding International Application PCT/SE2006/000615.

(Continued)

*Primary Examiner*—Timothy J Dole
*Assistant Examiner*—John Zhu
(74) *Attorney, Agent, or Firm*—WRB-IP LLP

(57) ABSTRACT

In a measurement instrument for measuring pollutants in a liquid, such as oil in water, the measurement instrument includes a main unit disposed in a first housing and a sensor unit disposed in a second housing. The housing, manufactured from an electrically insulating material, and an associated electric connection, are sealed against the passage of gas and liquid. The sensor unit has connections which are connected to a conduit system in which flows the liquid which is to be inspection measured. Sensors are further disposed in the sensor unit for emitting a measurement signal. The sensor unit and its electronics lack galvanic connection with electrically conductive components in the main unit, transfer of measurement signals between both of the units taking place by optical energy transfer, capacitative or inductive transfer. The housings have apertures for the transfer of measurement signals which are closed by non-electrically conductive foils which, when the main unit and the sensor unit are mounted together, abut against one another so they are protected against outer damage.

17 Claims, 5 Drawing Sheets

U.S. PATENT DOCUMENTS

| | | | | |
|---|---|---|---|---|
| 5,337,017 | A | * | 8/1994 | Ogawa ........................ 324/682 |
| 6,028,413 | A | * | 2/2000 | Brockmann ................. 320/108 |
| 7,159,456 | B2 | * | 1/2007 | Pechtold et al. ............... 73/200 |
| 7,372,914 | B2 | * | 5/2008 | Calvin ........................ 375/272 |
| 2004/0008036 | A1 | | 1/2004 | Schirmer et al. |
| 2007/0089956 | A1 | * | 4/2007 | Kozsar ........................ 191/10 |

OTHER PUBLICATIONS

International Search Report for corresponding International Application PCT/SE2006/000615.

Written Opinion of the International Searching Authority for corresponding International Application PCT/SE2006/000615.

* cited by examiner

MEASUREMENT INSTRUMENT

BACKGROUND AND SUMMARY

The present invention relates to a measurement instrument for measuring pollutants in a liquid, such as oil in water, comprising a main unit disposed in a first housing or casing, the main unit having a connection for electricity, and a sensor unit disposed in a second housing or casing, the second housing or casing having connections to a conduit system for that liquid which is to be measured, and sensor means for emitting a measurement signal.

In the pumping of bilge water from vessels, there are stringent restrictions relating to the maximum amount of pollutants, principally oil, which the bilge water may contain if it is to be permitted to pump the water overboard. The present invention relates, in an aspect thereof, to a measurement instrument which is intended for the continuous monitoring of the concentration of pollutants in such water and triggers an alarm or discontinues the pumping if the concentration becomes too high.

Apparatuses and instruments for the above-outlined purpose and of the type intimated by way of introduction are previously known in the art. In such measurement instruments, use has been made of an electric cable communication between the main unit and the sensor unit. This cable communication has, on the one hand, fed the sensor unit with the necessary electricity for its operation, but also fed back measurement signals from the sensor unit to the main unit where signal processing takes place and where measurement values are presented on a display.

If the sensor unit is to be dismounted, for example for calibration, cleaning or general service, it is naturally necessary that the cable communication between the sensor unit and the main unit be disconnected. Since the measurement instrument according to an aspect of the present invention is used in an extremely dirty marine environment, there is a major risk that water may penetrate in to both the main unit and the sensor unit when the cable communication is opened. In addition, there is also naturally a considerable risk of dirtying the contact surfaces in question. Since the currents that are transferred via the cable communication are slight, even a very insignificant level of dirt on the contact surfaces may cause major problems. As a result, it has not previously been possible to carry out replacement or calibration of the sensor unit without access to well-trained service personnel.

The fact that there is an electric communication between the main unit and the sensor unit entails that the electronics in the sensor unit will have an electric potential that is determined by the electric potential in the main unit and that does not necessarily correspond with the potential in the housing of the sensor unit or in the liquid passing through the sensor unit. This may give rise to galvanic currents with attendant corrosion problems.

It is desirable to design the measurement instrument intimated by way of introduction so that the drawbacks inherent in prior art technology are obviated. Thus, it is desirable to design the measurement instrument so that calibration, dismounting, cleaning and other maintenance are substantially facilitated. Further, it is desirable to design the measurement instrument so that problems involving dirtying, leakage and corrosion are eliminated.

According to an aspect of the present invention the measurement instrument intimated by way of introduction can be characterised in that both the first and the second housing or casing have mutually cooperating devices for inductive or capacitative energy transfer therebetween, and that the second housing or casing is secured on the first, or vice versa.

BRIEF DESCRIPTION OF THE ACCOMPANYING DRAWINGS

The present invention will now be described in greater detail hereinbelow, with reference to the accompanying Drawings. In the accompanying Drawings.

DETAILED DESCRIPTION

Figure 1:
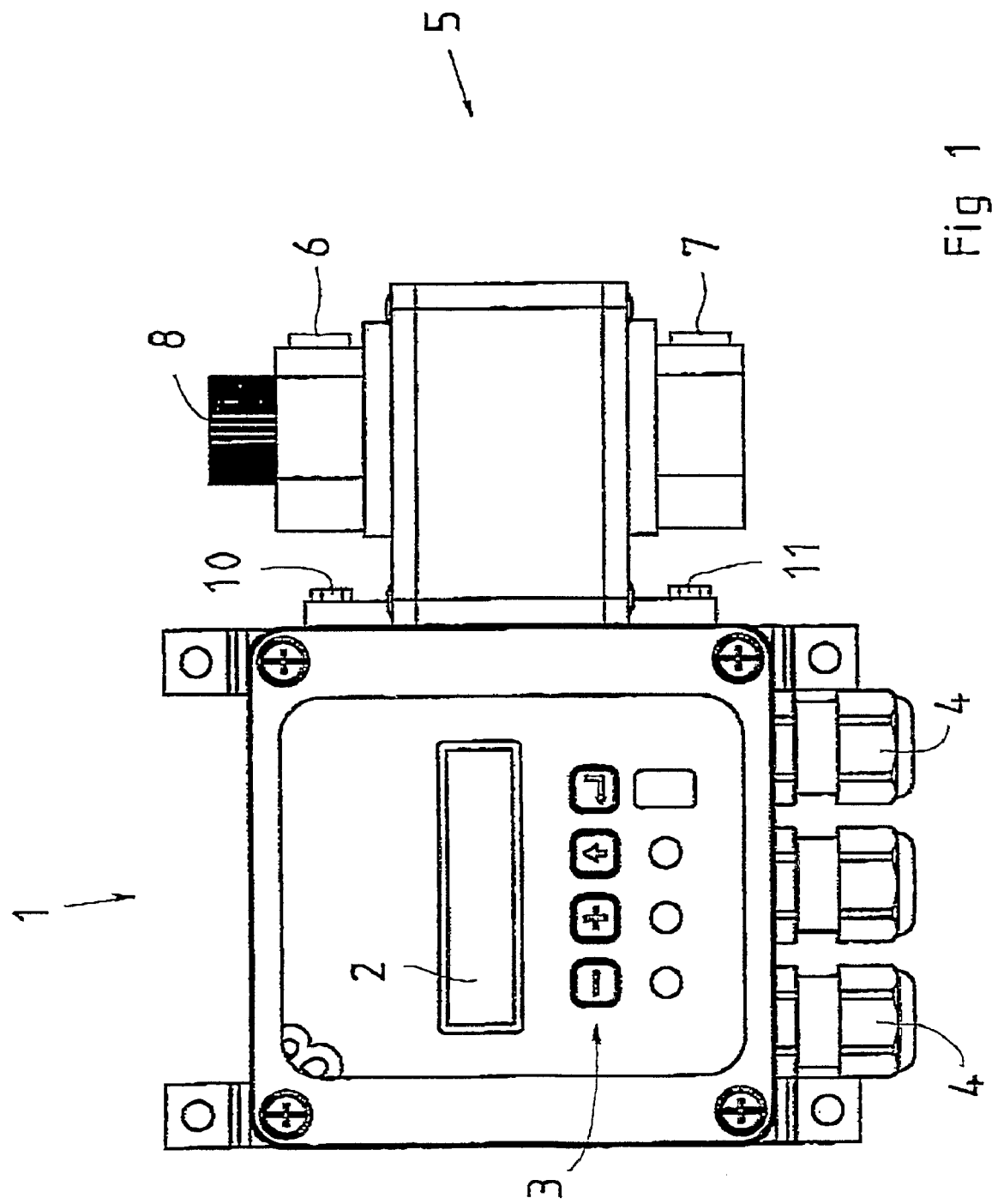
FIG. 1 is a front elevation of the measurement instrument according to an aspect of the present invention in the mounted state.

It will be apparent from FIG. 1 that the measurement instrument according to an aspect of the present invention has a main unit 1 with a display 2 and a button set or array 3 for operating the measurement instrument. Consequently, the main unit may also be considered as an operating unit or a presentation unit.

The main unit 1 has electric connections 4 for the supply of the electricity which the measurement instrument needs for its operation. Possibly, there may also be provided connections for data communication with a data system. Further, the connections may naturally also include the connections to a warning or alarm system or a flow signal which reflects the concentration of pollutants.

Since the subject matter of an aspect of the present invention is principally employed in an extremely dirty, wet and damp environment, as a rule on board a vessel, it is obvious that the electric connections 4 also include connections for protective earthing (grounding). This implies that the electronics interiorly in the main unit will have a potential which is determined by the protective earthing.

In the illustrated embodiment, the housing or casing which accommodates the main unit is manufactured from an electrically insulating material, preferably plastic. The housing or the casing is further sealed against both the passage of gas and liquid. This also applies to the electric connections 4.

It will further be apparent from FIG. 1 that the measurement instrument according to an aspect of the present invention has a sensor unit 5 with connections 6 and 7 to a conduit system in which flows the liquid which is to be monitored and inspection measured. It will further be apparent from the Figure that the sensor unit 5 has, on its upper side, a plug 8 which has a hermetically sealed connection to the sensor unit 5 and which, when it is removed, affords access to the measurement cell which is disposed interiorly in the sensor unit. It is thus possible, in a simple manner with the plug removed when necessary, to clean the measurement cell from any possible pollutants.

The sensor unit 5 has a housing or casing 9 which is produced from metal. Through the liquid connections 6 and 7 to the housing 9, the housing will have the same electric potential as the liquid flowing through the sensor unit. The fact that the housing 9 of the sensor unit is produced from metal also entails that a clear screening-off from external disruption is afforded to the electronics disposed interiorly in the sensor unit 5.

It will be apparent from FIG. 1 that the sensor unit 5 is secured on the main unit 1 by means of bolts 10, 11. These bolts 10 and 11 lack any electric communication with electronics and other electrically conductive components interiorly in the housing or casing of the main unit 1. As a result, the sensor unit 5 will be electrically insulated from the electronics which are disposed interiorly in the main unit. The sensor unit 5 and its electronics thus lack galvanic communication with electrically conductive components in the main unit 1.

According to an aspect of the present invention, both the housing of the main unit 1 and the sensor unit 5 have means for non-galvanic transfer of electricity between the two units. Further, there is provided a device for the transfer of measurement signals which also lacks galvanic communication with both of the units, hi practice therefore, signal transfer takes place via optical transfer.

The devices for non-galvanic energy transfer between the main unit 1 and the sensor unit 5 comprise, in the preferred embodiment, a transformer which has a first part 12 of the core with a primary winding 13 disposed in the main unit 1 and a second part 14 of the core with a secondary winding 15 disposed in the sensor unit 5. In this embodiment, the energy transfer is thus inductive. However, embodiments are also conceivable where the energy transfer takes place capacitatively, i.e. with the aid of a capacitor. The important feature in this context is that the energy transfer takes place entirely without conducting communication between the main unit 1 and the sensor unit 5.

Figure 2:
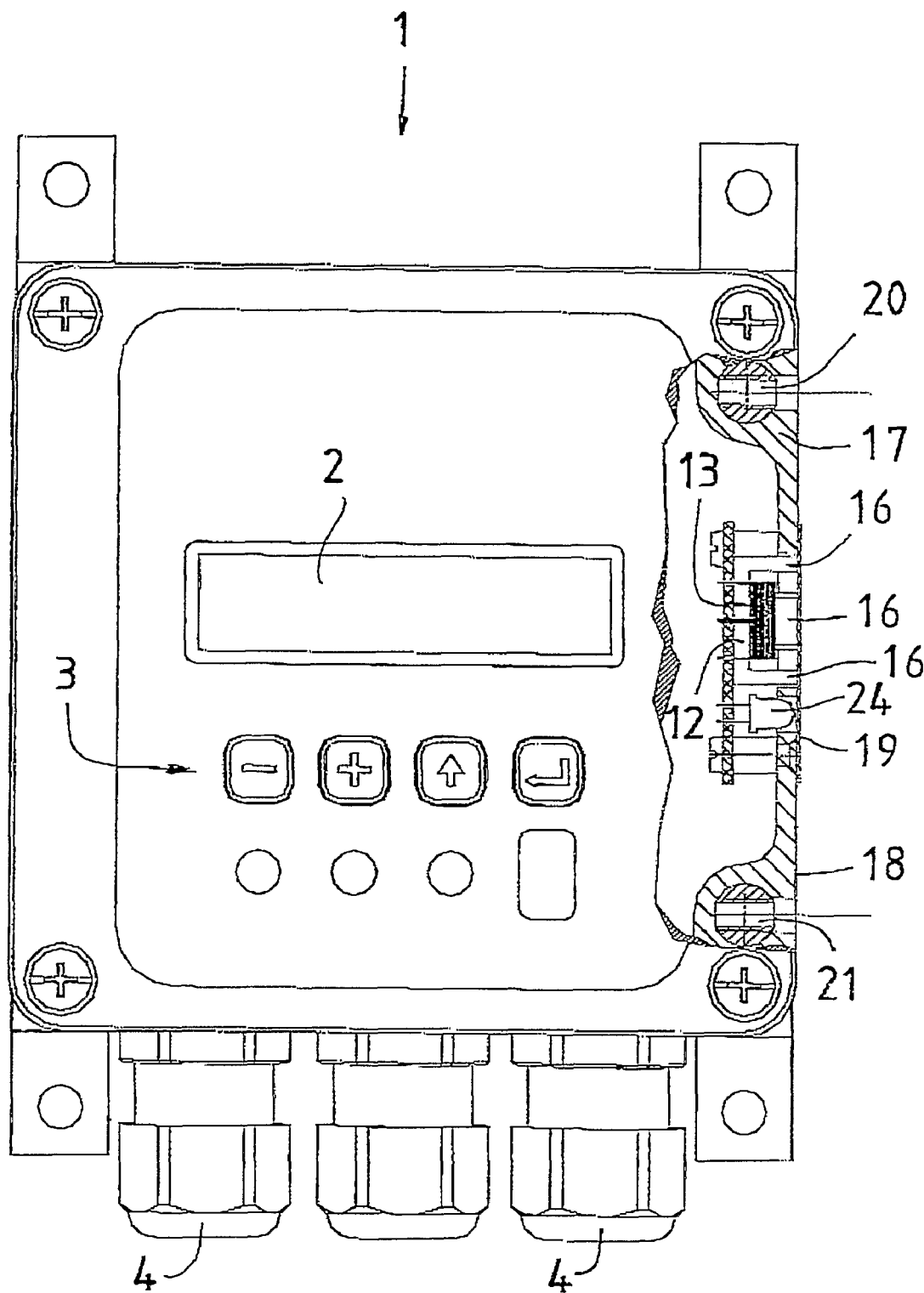
FIG. 2 shows a main unit included in the measurement instrument, partly cut-away for illustrating inner components.
Figure 3:
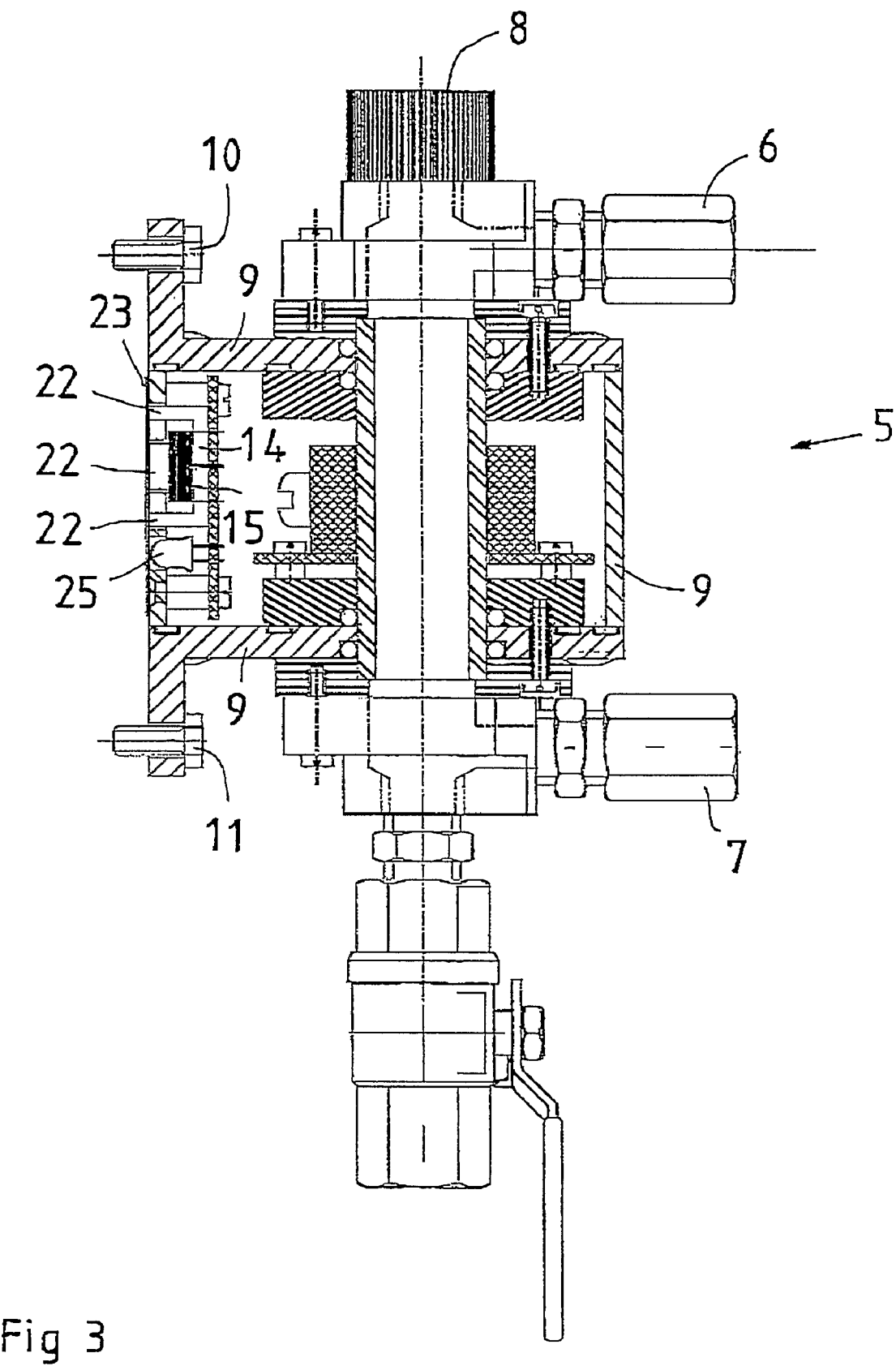
FIG. 3 is a vertical cross section through a sensor unit included in the measurement instrument according to FIG. 1.

It will be apparent from FIGS. 2 and 3 together that the above-mentioned transformer has a core with a first part 12 with the primary winding 13 in the main unit 1 and a second part 14 with the secondary winding 15 in the sensor unit 5. Each part of the core is in the form of an E.

It will be apparent from FIG. 2 that the first part 12 of the core has poles 16 which extend into apertures which are disposed in the wall of the housing 17 of the main unit. The poles 16 have planar end surfaces, pole surfaces, which lie flush with the outside 18 of the housing 17 of the main unit 1. The apertures that are provided in the housing 17 are closed by means of a foil or a thin layer of an electrically non-conductive material, preferably a plastic material. In FIG. 2, this foil is intimated at reference numeral 19. The foil 19 is preferably self-adhesive and seals against the outside of the housing 17 in such a manner that the seal will be both gas-tight and liquid-tight. Further, the pole surfaces of the poles 16 abut against the inside of the foil 19 and are fixedly secured with the aid of the adhesive of the foil which also sealingly fixes the foil on the outside of the housing. The area of the outside of the housing 17 around the foil 19 is preferably planar.

It will further be apparent from FIG. 2 that the housing 17 has, on its side facing towards the sensor unit 5, nuts 20 and 21 for accommodating those bolts 10 and 11 by means of which the sensor unit is fixed on the main unit. It will be apparent from FIG. 2 that these nuts 20 and 21 are embedded in the plastic material from which the housing 17 is manufactured. Thus, they are inaccessible from the inside of the housing 17.

In analogy with the main unit 1, the sensor unit 5 has, on the second part of the transformer core 14, poles 22 which are disposed in complete analogy with that described above. Further, the housing 9 of the sensor unit 5 has, in analogy with that which applies for the main unit 1, apertures into which the poles 22 extend. Also in analogy with the main unit 1, that area which has the apertures in the housing 9 is covered and sealed by means of a foil 23 or a thin, sheet-shaped material of electrically non-conductive material.

FIGS. 2 and 3 show, at reference numerals 24 and 25, respectively, means for optical transfer of measurement signals obtained in the sensor unit 5. In order for this optical transfer to be possible, both of the foils 19 and 23, respectively, have transparent windows in register with the transfer means 24 and 25. Other types of transfer, such as via radio, capacitatively or inductively, are possible, for example by superposing a signal on the transformer which feeds the sensor with energy.

When the sensor unit 5, as shown in FIG. 1, is fixedly bolted on the main unit 1, both of the foils 19 and 23 are clamped against one another for which reason they are completely protected against dirtying or mechanical action. In addition, as a result of the pretensioning between the sensor unit 5 and the main unit 1, transfer of the magnetic fields between the two cores 12 and 14 will take place with extremely slight losses, since both of the foils lie pressed against one another. Further, the suspension of the two parts 12 and 14 of the magnetic core may have a certain pretensioning so that further safety against magnetic losses is achieved.

Figure 4:
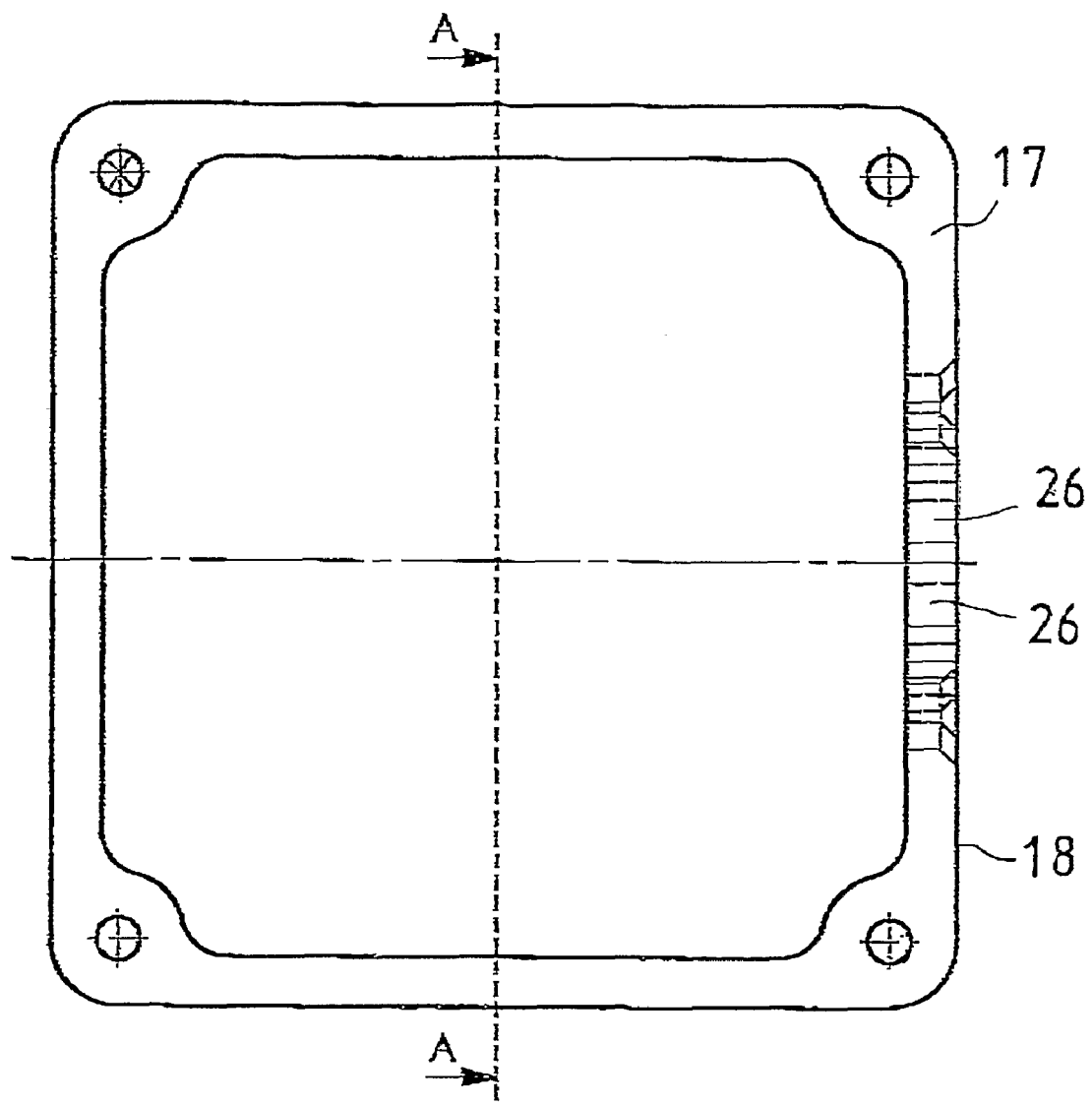
FIG. 4 is a vertical side elevation of the housing of the main unit.
Figure 5:
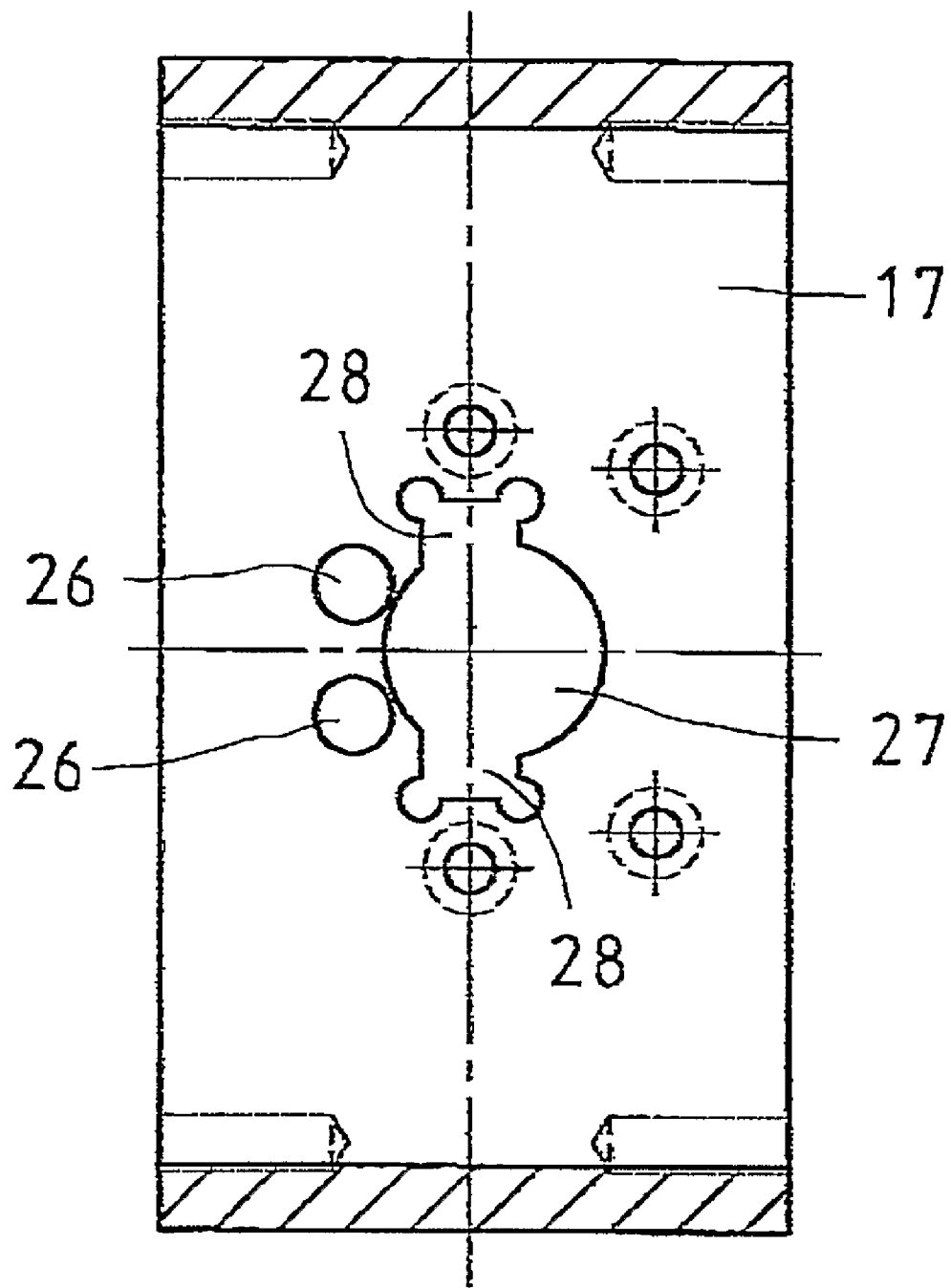
FIG. 5 is a section through the housing of the main unit taken along the section line A-A in FIG. 4.

It will be apparent from FIGS. 4 and 5 together that the housing 17 of the main unit 1 has two apertures 26 for the optical signal transfer and a larger aperture 27 for the first part 12 of the magnetic core.

The larger aperture 27 for the magnetic core has, at opposing edges (upside down in FIG. 5), recesses 28 which serve for guiding the poles 16 so that they will be accurately positioned in such a manner that the poles on the main unit 1 and the sensor unit 5 lie accurately centred in register with one another.

The housing 9 for the sensor unit 5 also has a corresponding design, with apertures, on the one hand for the second part 14 of the transformer core, and on the other hand for the optical signal transfer.

The present invention may be modified further without departing from the scope of the appended Claims.

What is claimed is:

1. A measurement instrument for measuring pollutants in a liquid, comprising a main unit disposed in a first housing, the main unit having a connection for electricity, and a sensor unit disposed in a second housing, the second housing having connections to a conduit system for that liquid which is to be measured, and a sensor for emitting a measurement signal, wherein both the first and the second housing have mutually cooperating devices for inductive or capacitative energy transfer therebetween, and the second housing or casing is secured to the first housing, wherein the first and the second housing have mutually corresponding apertures for the energy transfer, and the apertures are closed in gas-tight and liquid-tight fashion by foils or thin layers of electrically insulating material.

2. The measurement instrument as claimed in claim 1, wherein the foils or the thin layers abut with their outsides against one another when the second housing is secured to the first housing.

3. The measurement instrument as claimed in claim 2, wherein the surfaces of the housings on which the foils or the thin layers are applied are planar, the foils or the thin layers are pressed against one another when the second housing is secured to the first housing so that the foils or the thin layers are inaccessible and protected against outer damage and dirt.

4. The measurement instrument as claimed in claim 3, wherein the devices for inductive energy transfer comprise magnetic cores with pole surfaces, the magnetic cores extend into apertures in walls of the housings such that the walls of the housings are in abutment with the pole surfaces against the insides of the foils or the insides of the thin layers.

5. The measurement instrument as claimed in claim 4, wherein the foils or the thin layers are provided on their insides with adhesive which serves for positional fixing of the magnetic cores.

6. The measurement instrument as claimed in claim 4, wherein the foils or the thin layers have transparent portions and, in connection therewith, there are provided means for optical transfer of the measurement signals to the main unit.

7. The measurement instrument as claimed in claim 2, wherein the surfaces of the housings on which the foils or the thin layers are applied are planar, the foils or the thin layers are pressed against one another when the second housing is secured to the first housing so that the foils or the thin layers are inaccessible and protected against outer damage and dirt.

8. The measurement instrument as claimed in claim 7, wherein the foils or the thin layers have transparent portions and, in connection therewith, there are provided means for optical transfer of the measurement signals to the main unit.

9. The measurement instrument as claimed in claim 2, wherein the devices for inductive energy transfer comprise magnetic cores with pole surfaces, the magnetic cores extend into apertures in walls of the housings such that the walls of the housings are in abutment with the pole surfaces against the insides of the foils or the insides of the thin layers.

10. The measurement instrument as claimed in claim 9, wherein the foils or the thin layers are provided on their insides with adhesive which serves for positional fixing of the magnetic cores.

11. The measurement instrument as claimed in claim 9, wherein the foils or the thin layers have transparent portions and, in connection therewith, there are provided means for optical transfer of the measurement signals to the main unit.

12. The measurement instrument as claimed in claim 1, wherein the foils or the thin layers have transparent portions and, in connection therewith, there are provided means for optical transfer of the measurement signals to the main unit.

13. A measurement instrument for measuring pollutants in a liquid, comprising a main unit disposed in a first housing, the main unit having a connection for electricity, and a sensor unit disposed in a second housing, the second housing having connections to a conduit system for that liquid which is to be measured, and a sensor for emitting a measurement signal, wherein both the first and the second housing have mutually cooperating devices for inductive or capacitative energy transfer therebetween, and the second housing or casing is secured to the first housing, wherein the first and the second housing have mutually corresponding apertures for the energy transfer, and the apertures are closed in gas-tight and liquid-tight fashion by foils or thin layers of electrically insulating material, wherein the devices for inductive energy transfer comprise magnetic cores with pole surfaces, the magnetic cores extend into apertures in walls of the housings such that the walls of the housings are in abutment with the pole surfaces against the insides of the foils or the insides of the thin layers.

14. The measurement instrument as claimed in claim 13, wherein the foils or the thin layers are provided on their insides with adhesive which serves for positional fixing of the magnetic cores.

15. The measurement instrument as claimed in claim 13, wherein the foils or the thin layers abut with their outsides against one another when the second housing is secured to the first housing.

16. The measurement instrument as claimed in claim 15, wherein the surfaces of the housings on which the foils or the thin layers are applied are planar, the foils or the thin layers are pressed against one another when the second housing is secured to the first housing so that the foils or the thin layers are inaccessible and protected against outer damage and dirt.

17. The measurement instrument as claimed in claim 13, wherein the foils or the thin layers have transparent portions and, in connection therewith, there are provided means for optical transfer of the measurement signals to the main unit.

* * * * *